(12) United States Patent
Welle et al.

(10) Patent No.: US 8,701,483 B2
(45) Date of Patent: Apr. 22, 2014

(54) DEVICE FOR EMULSION MEASURING BY MEANS OF A STANDPIPE

(75) Inventors: Roland Welle, Oberwolfach (DE); Karl Griessbaum, Muehlenbach (DE)

(73) Assignee: VEGA Grieshaber KG, Wolfach (DE)

( * ) Notice: Subject to any disclaimer, the term of this patent is extended or adjusted under 35 U.S.C. 154(b) by 188 days.

(21) Appl. No.: 13/307,757

(22) Filed: Nov. 30, 2011

(65) Prior Publication Data

US 2013/0000400 A1     Jan. 3, 2013

Related U.S. Application Data

(60) Provisional application No. 61/423,771, filed on Dec. 16, 2010.

(30) Foreign Application Priority Data

Dec. 16, 2010 (EP) .................. PCT/EP2010/069997

(51) Int. Cl.
*G01F 23/28* (2006.01)

(52) U.S. Cl.
USPC .................. 73/290 V; 73/290 R; 73/298

(58) Field of Classification Search
USPC ..................... 73/290 R, 290 V, 298
See application file for complete search history.

(56) References Cited

U.S. PATENT DOCUMENTS

| | | | | |
|---|---|---|---|---|
| 2,787,160 A | * | 4/1957 | Van Valkenburg | 73/290 V |
| 3,394,589 A | * | 7/1968 | Tomioka | 73/290 V |
| 3,626,284 A | * | 12/1971 | Bak | 324/642 |
| 3,812,422 A | * | 5/1974 | De Carolis | 324/642 |
| 3,832,900 A | * | 9/1974 | Ross | 73/290 R |
| 3,834,233 A | * | 9/1974 | Willis et al. | 73/290 V |
| 4,852,054 A | * | 7/1989 | Mastandrea | 702/51 |
| 4,928,525 A | * | 5/1990 | Aderholt et al. | 73/290 V |
| 5,027,655 A | * | 7/1991 | Sweet | 73/290 V |
| 5,062,295 A | | 11/1991 | Shakkottai et al. | |
| 5,249,463 A | * | 10/1993 | Willson et al. | 73/290 R |
| 5,438,867 A | * | 8/1995 | van der Pol | 73/290 V |
| 5,686,658 A | * | 11/1997 | Boren | 73/49.2 |
| 5,847,567 A | * | 12/1998 | Kielb et al. | 324/642 |
| 5,898,308 A | * | 4/1999 | Champion | 324/643 |
| 5,969,666 A | * | 10/1999 | Burger et al. | 342/124 |
| 5,986,449 A | * | 11/1999 | Koski | 324/207.13 |

(Continued)

FOREIGN PATENT DOCUMENTS

| | | |
|---|---|---|
| DE | 10037715 A1 | 2/2002 |
| DE | 10044888 A1 | 4/2002 |

(Continued)

OTHER PUBLICATIONS

"Operating Instructions", VAGAFLEX 61, Document ID No. 31833, XP-002629700, 2 sheets.

(Continued)

*Primary Examiner* — David A Rogers
(74) *Attorney, Agent, or Firm* — Fay Kaplun & Marcin, LLP

(57) ABSTRACT

A measuring device is for determining a separating layer or a mixing ratio in a container. The measuring device comprises two fill-level measuring apparatuses that acquire the echo curves in a standpipe and outside the standpipe, respectively. Solely from these two echo curves the position of a virtual boundary layer or the mixing ratio of the two different liquids can be determined.

14 Claims, 8 Drawing Sheets

(56) References Cited

U.S. PATENT DOCUMENTS

| | | | |
|---|---|---|---|
| 6,184,818 B1* | 2/2001 | Meinel | 342/124 |
| 6,295,018 B1* | 9/2001 | Diede et al. | 342/124 |
| 6,445,192 B1* | 9/2002 | Lovegren et al. | 324/644 |
| 6,481,276 B1 | 11/2002 | Neuhaus et al. | |
| 6,644,114 B1* | 11/2003 | McEwan | 73/290 R |
| 6,701,783 B2 | 3/2004 | Fehrenbach et al. | |
| 6,895,815 B2* | 5/2005 | Adgie et al. | 73/290 V |
| 7,088,285 B2* | 8/2006 | Smith | 342/124 |
| 7,334,451 B1* | 2/2008 | Fauveau | 73/1.73 |
| 7,532,155 B2* | 5/2009 | Kleman et al. | 342/124 |
| 7,800,528 B2* | 9/2010 | Nilsson et al. | 342/124 |
| 7,924,216 B2* | 4/2011 | Delin | 342/124 |
| 8,018,373 B2* | 9/2011 | Edvardsson | 342/124 |
| 8,223,066 B2* | 7/2012 | Mouknatjou | 342/124 |
| 8,271,212 B2* | 9/2012 | Sai | 702/55 |
| 8,319,680 B2* | 11/2012 | Sai | 342/124 |
| 2001/0010171 A1 | 8/2001 | Atkinson | |
| 2002/0026828 A1* | 3/2002 | Fehrenbach et al. | 73/290 V |
| 2002/0100317 A1* | 8/2002 | Deserno et al. | 73/290 V |
| 2006/0225499 A1* | 10/2006 | Gravel et al. | 73/290 V |
| 2008/0210003 A1* | 9/2008 | Schulz | 73/290 V |
| 2009/0158839 A1* | 6/2009 | Spanke et al. | 73/290 V |
| 2010/0313654 A1 | 12/2010 | Malinovskiy et al. | |

FOREIGN PATENT DOCUMENTS

| | | |
|---|---|---|
| DE | 10325953 A1 | 12/2004 |
| DE | 102007061574 A1 | 6/2009 |
| WO | 2006/103200 A1 | 10/2006 |

OTHER PUBLICATIONS

"Guided Microwave", VEGAFLEX 60, XP-002629659, pp. 37-38.

* cited by examiner

DEVICE FOR EMULSION MEASURING BY MEANS OF A STANDPIPE

REFERENCE TO RELATED APPLICATIONS

This application claims the benefit of the filing date of PCT Patent Application Serial No. PCT/EP2010/069997 filed 16 Dec. 2010 and U.S. Provisional Patent Application Ser. No. 61/423,771 filed 16 Dec. 2010, the disclosure of both applications is hereby incorporated by reference.

TECHNICAL FIELD

The present invention relates to measuring all kind of fill levels, separating layers and emulsions. In particular, the invention relates to a measuring device that operates according to a transit time method, to a method for separating layer measuring and emulsion measuring, and to the use of the measuring device.

BACKGROUND INFORMATION

In fill-level sensors operating according to the FMCW or pulse-transit time method, electromagnetic or acoustic waves are emitted in the direction of a feed material surface. Subsequently, a sensor records the echo signals reflected by the feed material, the container internals and the container itself, and from these derives the respective fill level.

Fill-level sensors operating according to a transit time method may, for example, comprise sensors which determine the distance to a feed material surface with the use of ultrasound, radar, guided radar, FMCW radar, pulse-burst radar, CW radar or laser. Furthermore, all the sensors that emit a wave and subsequently receive and evaluate the components of said wave that are reflected by a feed material surface may be defined as fill-level sensors that operate according to a transit time method.

In the use of acoustic or optical waves the signal generated by the fill-level measuring device generally speaking propagates freely in the direction of the feed material surface to be measured. In the case of devices that use radar waves for measuring the feed material surface, both free propagation in the direction of the medium to be measured, and propagation in the interior of a waveguide that guides the radar waves from the fill-level measuring device to the medium can be considered. In the case of devices according to the principle of the guided microwave the high-frequency signals are guided along a waveguide towards the medium.

On the surface of the medium to be measured, some of the incoming signals are reflected, and after a corresponding transit time return to the fill-level measuring device. The non-reflected signal components enter the medium and propagate in it, according to the physical characteristics of the medium, in the direction of the container bottom. These signals are reflected by the container bottom and, after passing through the medium and the overlaid atmosphere, return to the fill-level measuring device.

Moreover, it is desirable to use fill-level measuring devices for separating layer measuring and also for emulsion measuring.

In the field of separating layer measuring, usually two different liquids are placed in a container. Because of the different densities of these at least two liquids, they de-mix in the container, provided adequately settled conditions are present, in other words provided the liquids are not prevented from de-mixing by an agitator or by some other equipment.

DE 10 2007 061 574 A1 describes a method for measuring emulsions by combining a measurement on the basis of a guided microwave with a capacitive measurement.

SUMMARY OF THE INVENTION

According to a first exemplary embodiment of the present invention, a measuring device, in particular an emulsion measuring device, is stated which operates according to a transit time method and can be used for determining at least one characteristic value relating to the fill level and/or to the mixing ratio of two or several liquids and/or for determining at least one characteristic value relating to the position of a virtual separating layer between two liquids in a container.

In this context, the term "virtual separating layer" refers to a separating layer between two different liquids, which separating layer would form if the emulsion comprising the two or several liquids were to disintegrate. This can, for example, happen when the entire liquid is not moved, for example not agitated, so that the individual liquids separate from each other.

The measuring device comprises a container for holding a first liquid and/or at least one second liquid. The density of the second liquid is lower than that of the first liquid.

The container comprises a first sub-region and a second sub-region, as well as one or several connections between these two sub-regions for exchanging liquid between the two sub-regions.

A first measuring apparatus is provided for acquiring a first echo curve that illustrates, i.e. determines the reflection conditions within the first sub-region. Furthermore, a second measuring device for acquiring at least a second echo curve is provided, which illustrates, i.e. determines the reflection conditions within the second sub-region.

Moreover, an evaluation unit is provided which is designed for determining at least one characteristic value relating to the position of the fill level and/or of an actually existing or virtual separating layer between the two different liquids of the feed medium in the second region of the container, or for determining at least one characteristic value relating to the composition of the mixture comprising the two or more different liquids in the second sub-region. To this effect the evaluation unit uses at least one characteristic value of the first echo curve, and at least one characteristic value of the second echo curve. The characteristic values of the first and second echo curves relate, for example, to total fill levels or to separating layer positions.

According to a further exemplary embodiment of the present invention, a method for fill-level measuring, separating layer measuring, and/or emulsion measuring is stated in which at least one characteristic value relating to the fill level of two different liquids in a first sub-region of a container is determined, and/or at least one characteristic value relating to the position of a separating layer between the two liquids in the first sub-region of the container is determined. Furthermore, determination of at least one characteristic value relating to the fill level of the two liquids in a second sub-region of the container takes place. This is followed by a calculation of the at least one characteristic value relating to the position of an actually existing or virtual separating layer between the two liquids in the second sub-region of the container with the use of the data obtained in the first two major measuring steps (in other words in the two preceding steps), as well as of the density ratio of the two liquids.

According to a further exemplary embodiment of the present invention, the use of a measuring device, described above and below, for determining at least one characteristic value relating to the fill level and/or to the position of an actually existing or virtual separating layer between two different liquids in a sub-region of a container is stated. Furthermore, the use of a measuring device, described above and below, for determining at least one characteristic value relating to the composition of a mixture comprising two or more different liquids in a container is stated.

It should be noted that the characteristics described above and below can be applied to all three aspects (device, method, use). In other words, characteristics which hereinafter have been described with reference to the method can also be implemented in the device and vice versa.

According to one embodiment of the invention, the first sub-region of the container is formed by the interior of a standpipe.

According to a further embodiment of the invention, the first sub-region of the container is formed by a bypass pipe of the container.

According to a further embodiment of the invention, the connection between the two sub-regions is formed by a first opening in the first sub-region of the container, which opening is situated near the container bottom, and by a second opening in the first sub-region of the container, which opening in the case of a properly filled container is situated above the feed media.

Thus, only two openings are provided in the first sub-region.

According to a further embodiment of the invention, the first sub-region and the connection between the two sub-regions are designed in such a manner that when a defined quantity of liquid is added in the second sub-region, the level of a liquid column forming in the first sub-region differs from the level of a liquid column in the second sub-region.

This can be achieved in that an added lighter-weight liquid cannot reach (or at least not in a significant quantity) the first sub-region through the lower connection.

According to a further embodiment of the invention, the first measuring apparatus and the second measuring apparatus are identical devices. For example they are fill-level measuring devices, for example fill-level radars, ultrasound fill-level measuring devices, or devices operating according to the principle of the guided microwave.

According to a further embodiment of the invention, at least one of the two measuring apparatuses is a device that emits an electromagnetic transmission signal or an acoustic transmission signal.

According to a further embodiment of the invention, the first measuring apparatus operates according to the principle of the guided microwave and comprises an inner guide arranged within the first sub-region, wherein the inner guide and a wall of the first sub-region form a coaxial guide so that the echo curve within the first sub-region is determined by means of the coaxial guide formed by the inner guide and the wall of the first sub-region.

According to a further embodiment of the invention, the measuring device is, furthermore, designed for acquiring and issuing at least one characteristic value relating to the fill level in the second sub-region of the container. It is thus possible to determine not only mixing ratios or separating layer positions.

According to a further embodiment of the invention, determining the at least one characteristic value relating to the position of an actually existing or virtual separating layer between the two different liquids of the feed medium in the second region, or determining the at least one characteristic value relating to the composition of the mixture comprising the two different liquids takes place without the aid of capacitive measuring.

Only the acquired echo curves are necessary to determine the mixing ratio of the two or more liquids in the second sub-region of the container or to determine the position of a virtual separating layer.

According to a further embodiment of the invention, determining the density ratio of the two liquids takes place by means of a measurement in which the at least one characteristic value relating to the fill level of the two different liquids and the at least one characteristic value relating to the position of the separating layer between the two liquids in the first and the second sub-regions of the container is determined.

According to a further embodiment of the invention, mixing the two liquids takes place in the second sub-region after the density ratio has been determined and before the two major measuring steps have been carried out.

Below, exemplary embodiments of the invention are described with reference to the figures.

DETAILED DESCRIPTION

The illustrations in the figures are diagrammatic and not to scale.

Figure 1:
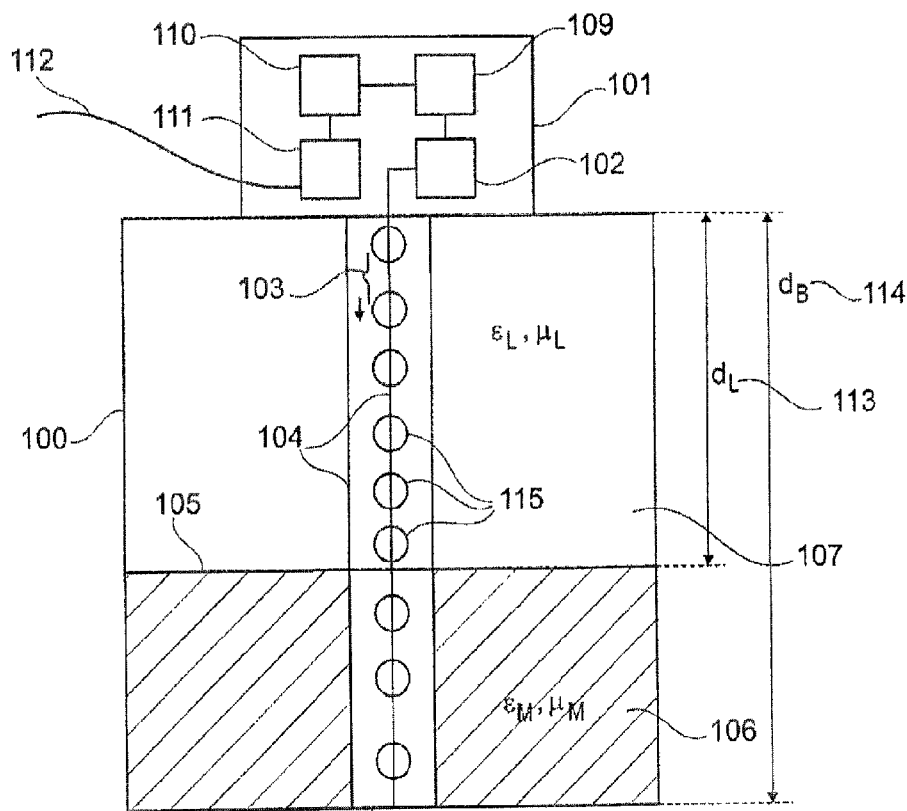
FIG. 1 shows an arrangement for fill-level measuring.

FIG. 1 shows an arrangement for fill-level measuring. It is desirable that modern fill-level measuring devices can not only determine the total fill level in the container but also the position of the separating layer that forms between two different media.

The present invention utilizes electromagnetic waves. In this arrangement the situation is utilized in which part of the signals emitted by the fill-level measuring device is reflected by the surface of the uppermost liquid, while the remaining component enters this uppermost liquid layer and after a corresponding transit time impinges on the separating layer between the two liquids. On this separating layer, again, part of the signal energy is reflected, and after a corresponding transit time returns to the fill-level measuring device. Any signal energy still remaining also passes through the second liquid, and is finally reflected by the container bottom.

The fill-level measuring device receives the signals reflected on various locations, and from them determines the distance to the feed material according to known methods.

The conditions become more difficult when as a result of continuous movement of the media in a container, de-mixing of the different liquids is prevented or can take place only partially. Due to the incorrect position of a forming separating layer or due to total absence of separating layer formation between the media, it is not possible to measure the emulsion exclusively by means of electromagnetic waves. At present, other measuring methods are used for this purpose (pressure, capacitive measuring) or combinations of radar fill-level measuring and other methods.

The determined distance to the feed material is provided towards the outside. The provision can be implemented in analog form (for example with the use of a 4.20 mA interface) or in digital form (for example with the use of a field bus).

The fundamental design of radar fill-level sensors is described in detail in the book "Füllstandsmessung mit Radar. Leitfaden für die Prozessindustrie" (ISBN 3-00-008216-6) by Peter Devine.

The following description concentrates on the very important area of fill-level measuring by means of electromagnetic waves. It should, however, be pointed out that even with the use of acoustic waves, measuring of the feed material surface or of a separating layer forming between two different media is possible. The propagation of acoustic waves is also influenced by the different density ratios of media to be passed through. It is thus possible for the average person skilled in the art to transpose the ideas presented below, on the topic of fill-level measuring, separating layer measuring and/or emulsion measuring, from the case of application of electromagnetic waves to the case of application of acoustic waves.

In the devices for fill-level measuring, separating layer measuring and/or emulsion measuring various methods can be used for determining the total fill level and/or the position of a separating layer between two different media.

The implementation form presently described is based on an arrangement which determines the fill level and/or the position of a separating layer according to the principle of the guided microwave. However, it is also possible to implement corresponding devices according to the measuring principles set out above, in particular with the use of freely radiating radar waves.

FIG. 1 shows an exemplary arrangement for fill-level measuring. The container 100 contains a liquid 106 up to a filling height $d_B$-$d_L$. In the first assumption the space above the liquid 107 comprises air.

A fill-level measuring device 101 operating according to the principle of the guided microwave generates an electromagnetic pulse 103 by means of a high-frequency unit 102 and couples said pulse 103 into a waveguide 104, after which this pulse propagates in the interior of the waveguide almost at the speed of light in the direction of the feed material surface 105 to be measured.

In the present example the waveguide 105 shown is designed in the form of a coaxial guide. However, any waveguides described in the literature can be considered, thus in particular single-wire or multiple-wire lines can be used.

The coaxial guide 104 normally used for fill-level measuring comprises a pipe that has holes 115, spaced apart from each other so as to be equidistant, that make it possible for the liquid 101 to be measured to enter the region between the outer guide (pipe), and the inner guide.

The feed material surface 105 reflects part of the incoming signal energy, whereupon the reflected signal component propagates along the waveguide 104 back to the fill-level measuring device 101. The non-reflected signal component enters the liquid 106 and propagates in it at greatly reduced speed along the waveguide 104. The speed $c_{Medium}$ of the electromagnetic wave 103 inside the liquid 106 is determined by the material characteristics of the liquid 106:

$$c_{Medium} = \frac{c_0}{\sqrt{\varepsilon_R \cdot \mu_R}}$$

wherein $c_0$ denotes the speed of light in the vacuum, $\varepsilon_R$ denotes the permittivity value of the liquid, and $\mu_R$ denotes the permeability value of the liquid. At the lower end 108 of the waveguide 104 the remaining signal component is also reflected and after a corresponding transit time returns to the fill-level measuring device 101. In the fill-level measuring device the incoming signals are processed by means of the high-frequency unit 102 and are, preferably, transformed to a lower-frequency intermediate frequency. By means of an analog-digital converter unit 109 the analog echo curves, which are provided by the high-frequency unit 102, are digitized and made available to an evaluation unit 110. The evaluation unit 110 analyzes the digitized echo curve and, based on the echoes contained therein, according to predeterminable known methods determines that echo which has been generated by the reflection from the feed material surface 105. Moreover, the evaluation unit 110 determines the precise distance to this echo. Furthermore, the precise distance to the echo is corrected in such a manner that influences which the overlaid gas atmosphere 107 has on the propagation of the electromagnetic waves are compensated. The compensated distance to the feed material 113, which distance has been calculated in this manner, is provided to an output unit 111 which further processes the particular value according to the specifications of the user, for example by linearization, offset correction, conversion to a filling height $d_B$-$d_L$. The processed measured value is provided towards the outside on an external communication interface 112. Any established interfaces can be used for such provision, in particular 4.20 mA current interfaces, industrial field buses such as HART, Profibus, FF, or also computer interfaces such as RS232, RS485, USB, Ethernet, FireWire.

Figure 2:
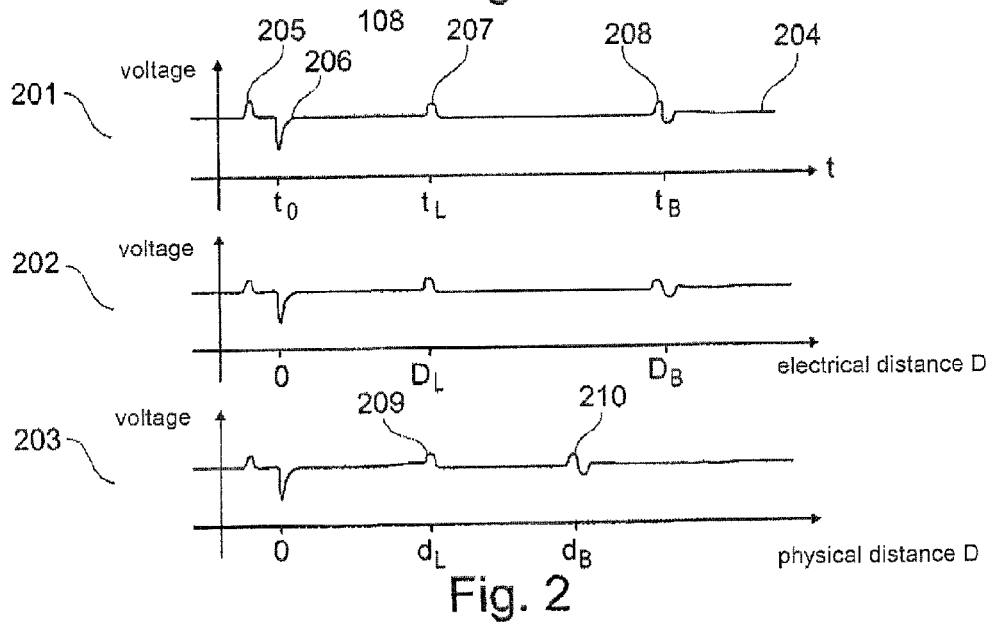
FIG. 2 shows the evaluation of echo signals.

FIG. 2 again in detail illustrates important steps which in the context of echo signal processing in the evaluation unit 110 are used for compensating the influence of various media.

Curve 201 first shows the echo curve 204 which has been acquired by the analog-digital converter unit 109 over time. The echo curve first comprises the transmission pulse 205. A short time later, at the point in time $t_0$, a first reflection 206 is acquired which has been caused by coupling the high-frequency signal into the waveguide 104. A further reflection 207 is derived from the feed material surface 105 and is acquired at the point in time $t_L$. Finally, the echo 208 generated by the lower end 108 of the waveguide 104 is acquired at the point in time $t_B$.

In a first processing step the time-dependent curve 201 is transformed to a distance-dependent curve 202. During this transformation it is assumed that the acquired curve has formed exclusively by propagation in a vacuum. By multiplication with the speed of light in the vacuum, the ordinate of the illustration 201 is converted to a distance axis. Furthermore, calculating an offset results in the echo 206 caused by coupling-in the high-frequency signal obtaining the distance value of 0 m.

The second illustration 202 shows the echo curve as a function of the electrical distance D. The electrical distance corresponds to the distance which an electromagnetic wave in a vacuum covers in a given time. The electrical distance does not take into account any influences of a medium, which influences may possibly result in slower propagation of the electromagnetic waves. The curve 202 thus represents a non-compensated-for echo curve that is, however, connected to locations.

In the present description electrical distances are always designated by upper case characters D, whereas physical distances that can be measured directly on the container are designated by lower case characters d.

It may, furthermore, be possible to fully compensate the echo curve of the illustration 202. The third illustration 203 shows a fully compensated echo curve. In order to obtain an illustration of the echo above the physical distance, in the present case the influence of the overlay medium 107 in the region between locations 0 and $D_L$ (curve 202) needs to be taken into account. The electrical distance indications of the abscissa between 0 and $D_L$ need to be converted to physical distance indications according to the following context:

$$d_i = \frac{D_i}{\sqrt{\varepsilon_L \cdot \mu_L}}$$

Since $\in_{Luft}$ and $\mu_{Luft}$ in good approximation correspond to the value 1, for this section no correction is required. However, the electrical distance indications of the abscissa between $D_L$ and $D_B$ need to be converted to physical distance indications according to the following context:

$$d_i = \frac{D_i}{\sqrt{\varepsilon_M \cdot \mu_M}}$$

The third illustration 203 finally shows the corrected gradient. Both the distance to the echo 209 of the feed material surface and the distance of the echo 210 generated by the lower end 108 of the waveguide 104 correspond to the distances 113, 114 that can be measured on the container 100.

It should be pointed out that within the context of signal processing, conversion to curve 202, in other words determination of the electrical distances of various echoes, is carried out in the device in relation to all the echoes. Conversion of the echo curve to a compensated echo curve is, generally speaking, not carried out because correction of a single fill-level value is sufficient.

Figure 3:
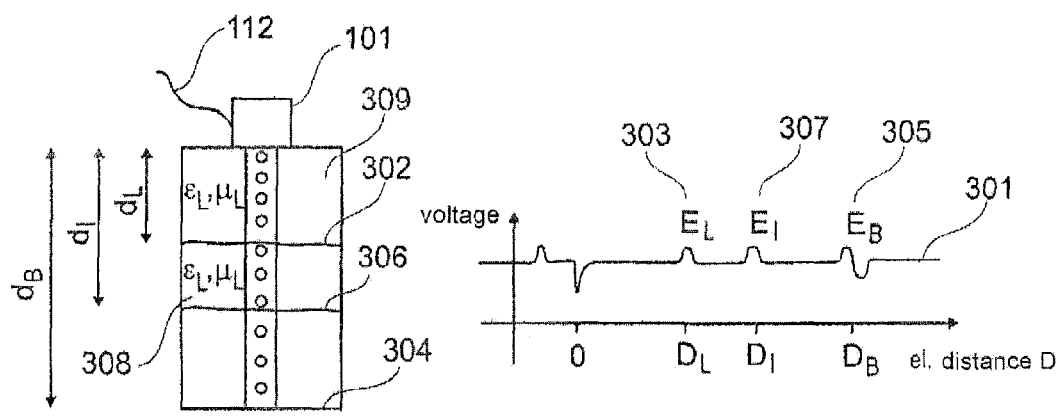
FIG. 3 shows an arrangement for fill-level measuring and separating layer measuring.

FIG. 3 shows an arrangement for fill-level measuring and separating layer measuring. The fill-level measuring device 101 first acquires the echo curve 301, which apart from the echo ($E_L$) 303 generated by the feed material surface 302 also comprises an echo ($E_I$) 307 generated by the separating layer 306. For reasons of completeness the echo curve 301 also comprises an echo ($E_B$) 305 generated by the container bottom 304, which echo ($E_B$) 305 in practical applications can be detected only on extremely rare occasions because as a result of the reflection on the surface 302 and on the separating layer 306 almost the entire energy of the signal emitted by the fill-level measuring device is reflected.

With the assumption of overlaid air ($\in_{Luft}=\mu_{Luft}=1$) or correspondingly deviating parameterization by the user, from the electrical distance to the feed material surface, which electrical distance has been determined by the logic unit 110, the physical distance results as follows:

$$d_L = \frac{D_L}{\sqrt{\varepsilon_L \cdot \mu_L}}$$

Furthermore, according to the state of the art it is a prerequisite that $\in_I$ and $\mu_I$, in other words the permeability value and the permittivity value of the separating layer medium 308 are known by user input. Thus the distance to the separating layer is as follows:

$$d_I = d_L + \frac{D_I - D_L}{\sqrt{\varepsilon_I \cdot \mu_I}}$$

It is immediately evident that in practical implementation the method causes problems. Firstly, the permittivity values and the permeability values of both the overlay atmosphere 309 and of the separating layer medium 308 must be known in advance or must be manually input by the user. At the very least this results in a lack of convenience of operation, and causes great problems whenever the characteristics of the overlay medium 309 and/or of the separating layer medium 308 are subjected to changes during the transit time. These characteristics can fluctuate not only as a result of filling with some other medium, but also if the material characteristics depend on external influences such as pressure and/or temperature.

The method described above can have weaknesses when the distance to the separating layer 401 is only insignificantly larger than the distance to the surface 402 of the total fill level.

Figure 4:
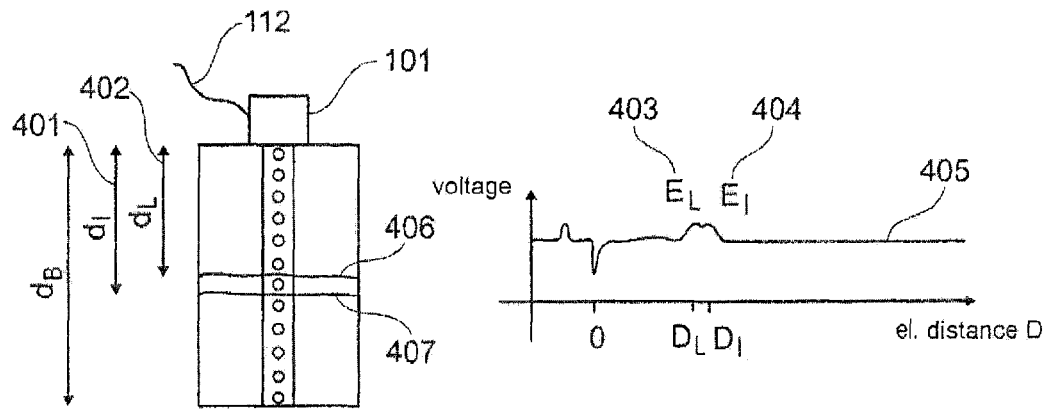
FIG. 4 shows fill-level measuring and separating layer measuring in the case of unfavorable layer thicknesses.

FIG. 4 illustrates this set of problems. The echo curve 405 acquired by the sensor 101 no longer permits reliable separation of the echo ($E_L$) 403 generated by the surface 406 from the echo ($E_I$) 404 generated by the separating layer 407, which results in large inaccuracies in the value determined in relation to the distance from the separating layer 401.

In a conventional container such measuring according to the radar principle or the principle of the guided microwave may under some circumstances become totally impossible whenever the formation of a separating layer is prevented.

Figure 5:
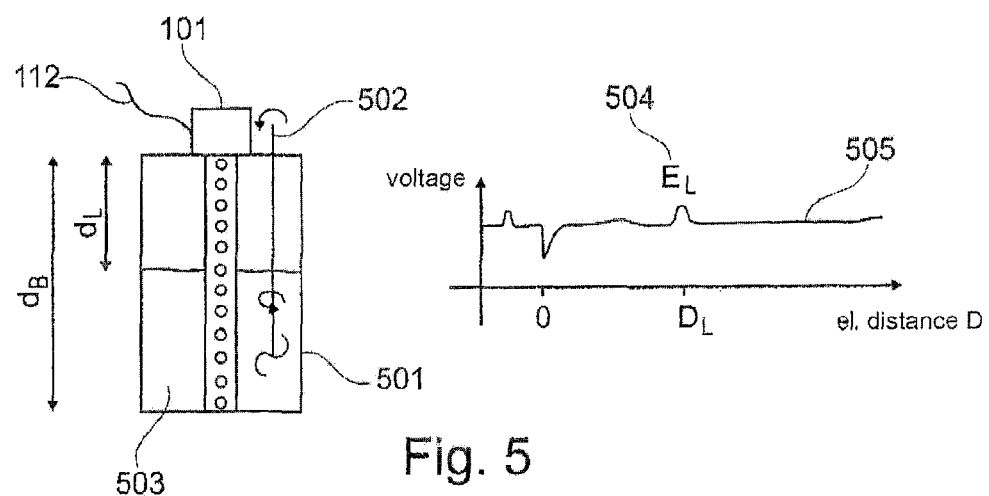
FIG. 5 shows emulsion measuring with a guided microwave.

FIG. 5 shows a corresponding arrangement. In the container 501 there is an agitator 502 which continuously prevents the emulsion 503 from de-mixing and from forming a separating layer. The echo curve 505 acquired by the fill-level measuring device 101 consequently includes only one echo ($E_L$) 504, from the position of which the total fill level $d_L$ 402 can be deduced. Determining the mass fraction or volume fraction of the components mixed in the emulsion 503 is not possible with the use of a method that is purely based on electromagnetic waves.

Emulsions in containers can be measured by means of several sensors or a combination of several measuring methods in a device. This often requires increased expenditure for devices or components and extensive input of characteristic values relating to materials.

Furthermore, separating layers and/or emulsions can be measured in specially designed containers.

Figure 11:
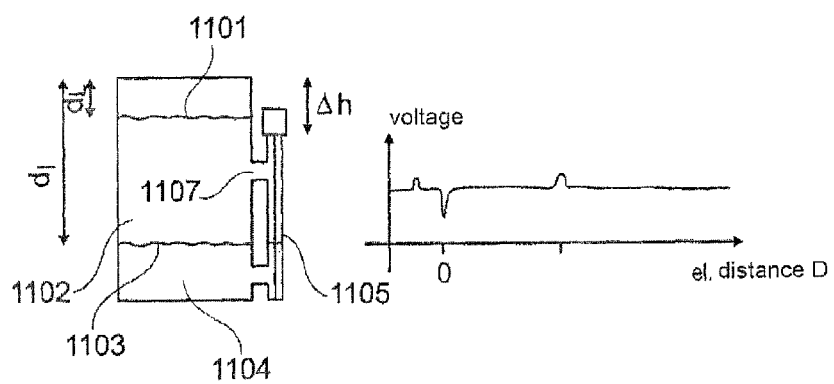
FIG. 11 shows a device for separating layer measuring as well as a corresponding echo curve.

FIG. 11 shows a corresponding arrangement comprising a bypass pipe 1105. Measuring makes it possible to continuously determine the position of a separating layer 1103 between a lower medium 1104 and an upper medium 1102, provided the user ensures that the position of the total fill level 1101 is always above the upper connection 1107. The bypass pipe 1105 is continuously full of the two media up to the upper rim. Simultaneous determination of the position of the total fill level 1101 and of the position of the separating layer 1103 is not possible with this arrangement.

Figure 12:
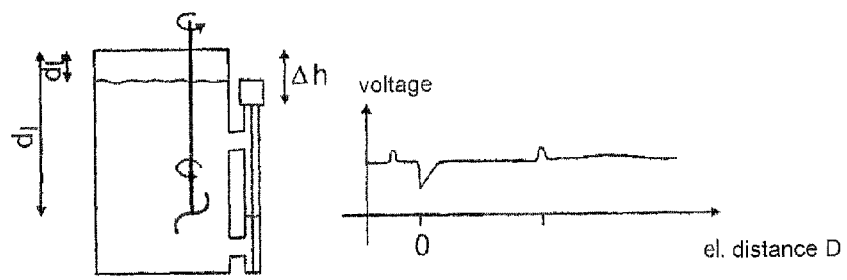
FIG. 12 shows a device for emulsion measuring as well as a corresponding echo curve.

FIG. 12 shows the circumstances of an arrangement according to FIG. 11 with the use of an agitator and the formation of an emulsion. This arrangement is associated with disadvantages relating to additional expense in the construction of the container, the absence of simultaneous determination of the fill level, and the necessity of having to keep the container in the region of the upper connection 1107 always full of the upper medium 1102.

Figure 6:
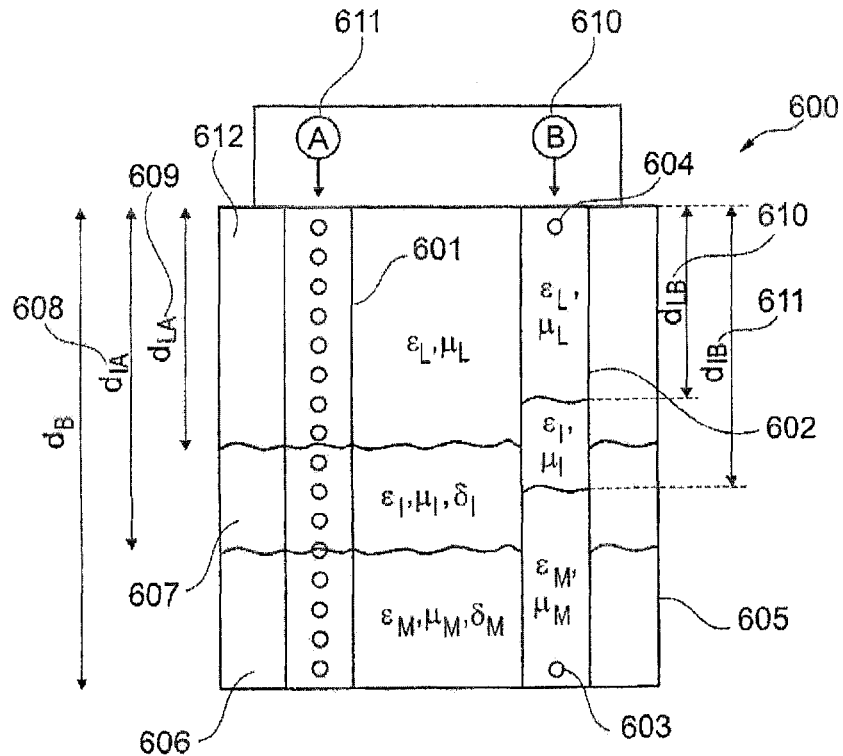
FIG. 6 shows an arrangement of a measuring device according to an exemplary embodiment of the invention.
Figure 7:
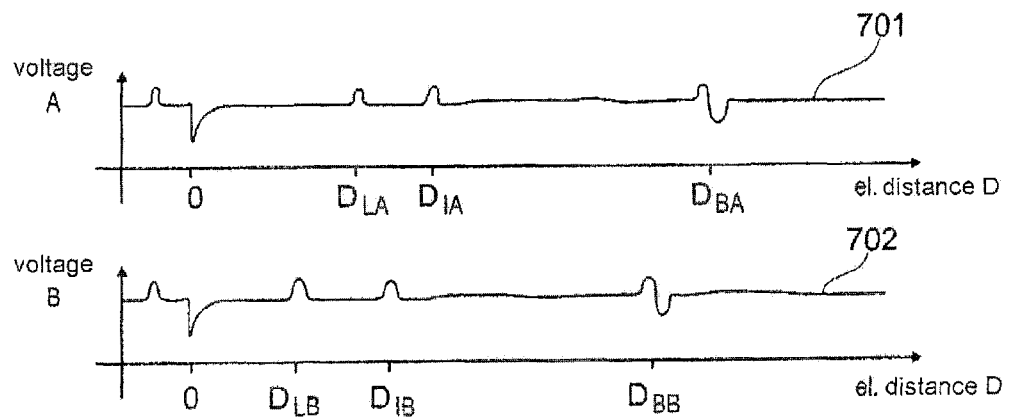
FIG. 7 shows the acquired echo signals according to an exemplary embodiment of the invention.

Below, further exemplary embodiments of the invention are described:

FIG. 6 shows a device according to an exemplary embodiment of the invention. The device comprises a first coaxial guide 601 whose design is identical to the hitherto used forms 104. Moreover, the device comprises a second coaxial guide 602 that differs from the hitherto-used coaxial guides for separating layer measuring in such a manner that it comprises an opening along its longitudinal extension only on its lower end 603 and on its upper end 604. Otherwise the resulting standpipe 602, which from an electrical point of view serves as a coaxial guide, is closed. The two coaxial guides form the two measuring channels A and B of a measuring device 600.

If the container 605 is filled with two different media 606, 607, as a result of the special design of the standpipe B 602 various levels result in terms of the position of the separating layer and of the total fill level. In the container 605 and thus also in the pipe 601 of the measurement A the value relating to the physical distance $d_{IA}$ 608 to the separating layer differs from the value of the physical distance $d_{IB}$ 611 to the forming separating layer in the pipe 602 of the measurement B. Likewise, the value relating to the physical distance $d_{LA}$ 609 to the media surface in the container differs from the value relating to the physical distance $d_{LB}$ 610 to the forming liquid surface in the pipe of the measurement B. The correlations that describe the respective levels in the container and in the pipe of the measurement A under the assumption of an identical hydrostatic pressure at the container bottom can easily be derived by the average person skilled in the art.

In the context of a teach-in phase or in the context of normal measuring cycles the fill-level measuring device according to the invention then carries out two separate measurements A and B, either simultaneously or consecutively. The reflections of measurement A, which is carried out by means of the coaxial guide 601, are acquired by the fill-level measuring device and are further analyzed, in an evaluation unit 110, by the fill-level measuring device in the form of a digitized echo curve 701. The evaluation unit 110 determines in particular the electrical distance $D_{LA}$ to the surface of the medium to be measured; the electrical distance $D_{IA}$ to the separating layer; and, if possible based on the amplitude ratios, the electrical distance $D_{BA}$ to the bottom echo according to known methods. Furthermore, the reflections of the measurement B, which measurement is carried out by means of the coaxial guide 602, is acquired by the fill-level measuring device and is further analyzed in the form of a further digitized echo curve 702 in an evaluation unit 110. The evaluation unit 110 again determines the electrical distance $D_{LB}$ to the surface of the medium to be measured in the pipe B; the electrical distance $D_{IB}$ to the separating layer in the pipe B; and, if possible based on the amplitude ratios, the electrical distance $D_{BB}$ to the bottom echo in pipe B according to known methods.

Based on the values determined it is possible to draw the following conclusions relating to the media characteristics of the separating layer medium:

$$\varepsilon_I \cdot \mu_I = \left( \frac{(D_{BB} - D_{IB}) \cdot (D_{IA} - D_{LA}) - (D_{BA} - D_{IA}) \cdot (D_{IB} - D_{LB})}{(D_{BB} - D_{IB}) \cdot \left(d_B - \frac{1}{\sqrt{\varepsilon_L \cdot \mu_L}} \cdot D_{LA}\right) - (D_{BA} - D_{IA}) \cdot \left(d_B - \frac{1}{\sqrt{\varepsilon_L \cdot \mu_L}} \cdot D_{LB}\right)} \right)^2$$

The above equation shows that apart from the characteristic values determined from measurement A and measurement B both the container height $d_B$ and the media characteristics $\varepsilon_L \cdot \mu_L$ of the overlaid atmosphere 612 are obtained. The container height $d_B$ can be permanently stored in the fill-level measuring device 600 at the factory because said container height $d_B$ is known on the basis of the manufactured length of the coaxial guides. In terms of the media characteristics $\varepsilon_L \cdot \mu_L$ of the overlaid atmosphere 612 in a multitude of practical applications a replacement value of 1 can be used, which corresponds to an overlay of air. If the overlay medium differs from this assumption, then either a user input or automatic determination can be considered.

Furthermore, it is possible to calculate the media characteristics of the lower medium:

$$\varepsilon_M \cdot \mu_M = \left( \frac{D_{BB} - D_{IB}}{d_B - \frac{1}{\sqrt{\varepsilon_L \cdot \mu_L}} \cdot D_{LB} - \frac{1}{\sqrt{\varepsilon_I \cdot \mu_I}} (D_{IB} - D_{LB})} \right)^2$$

This characteristic value can, in particular, be used to advantage for measuring bottom echoes, but it is not absolutely necessary to the core aspect of the invention.

Determining the media characteristics of the separating layer medium and/or of the lower medium needs to take place only once, at the time of commissioning or if there is a change of media. Since, generally speaking, at these points in time the container 605 is far from full, there is a good chance that the required characteristic values $D_{BA}$ and $D_{BB}$ can be measured by means of the echo curves 701 and 702 since, as a result of the thin layers, the attenuating characteristics of the media are very much limited. As an alternative it may also be possible to determine the media characteristics of the separating layer medium by way of user input.

Furthermore, on the basis of the determined characteristic values it is possible to determine in an automated manner the ratio of density $\rho_M$ of the lower medium 606 to density $\rho_I$ of the upper medium 607:

$$\kappa = \frac{\rho_M}{\rho_I} = 1 - \frac{1}{1 + \sqrt{\frac{\varepsilon_L \cdot \mu_L}{\varepsilon_I \cdot \mu_I}} \cdot \left(\frac{D_{IA} - D_{IB}}{D_{LA} - D_{LB}} - 1\right)}$$

The values determined in relation to $\varepsilon_I \cdot \mu_I$ and to $\kappa$ are application-specific constants that are calculated once by the fill-level measuring device, during commissioning, and that are stored in the storage device of the fill-level measuring device. It may also be possible to determine the values on an ongoing basis and in this way to be able to adapt measuring in an automated manner to changing media 606, 607. In principle it may also be possible to have the values relating to $\in_r \cdot \mu_r$ and the density ratio κ entered by the user.

Based on the application-specific constants determined, a normal measuring cycle can then take place.

Figure 8:
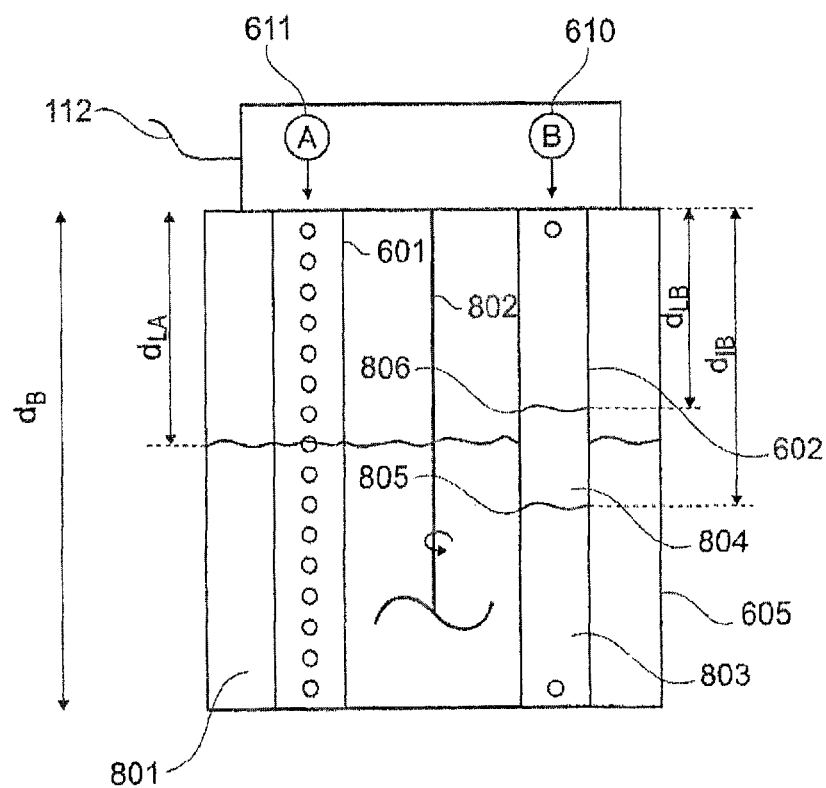
FIG. 8 shows an arrangement for emulsion measuring according to a further exemplary embodiment of the invention.
Figure 9:
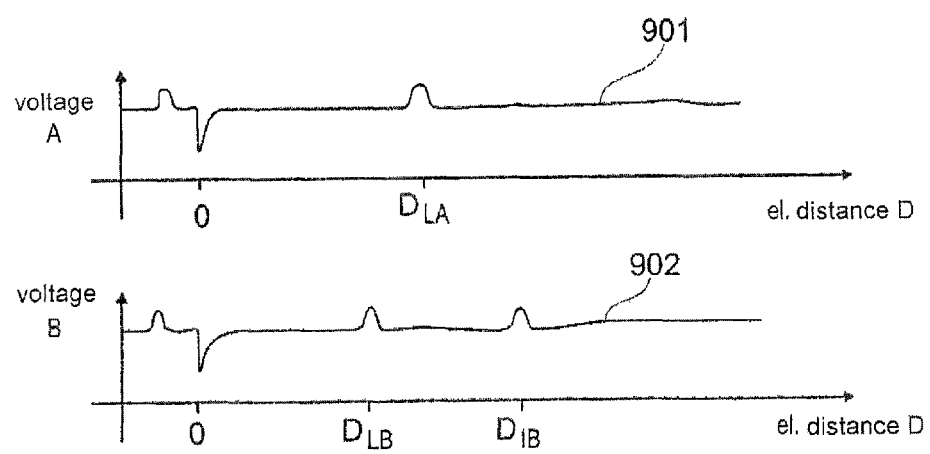
FIG. 9 shows the echo signals during emulsion measuring according to an exemplary embodiment of the invention.

FIG. 8 shows a device at the time of measuring an emulsion. As a result of the operation of an agitator 802 the emulsion 801 comprising the lower medium 606 and the upper medium 607 is constantly prevented from de-mixing and forming a separating layer. In the standpipe of measurement B the components 803, 804 of the emulsion fully de-mix because of the absence of any turbulence in that location, thus forming a clean separating layer 805 as well as a liquid surface 806 which localizes the fill level or total fill level of the measurement B.

The fill-level measuring device according to the invention then carries out two separate measurements A and B, either simultaneously or consecutively. The reflections of measurement A, which is carried out by means of the coaxial guide 601, are acquired by the fill-level measuring device and are further analyzed, in an evaluation unit 110, by the fill-level measuring device in the form of a digitized echo curve 901. The evaluation unit 110 determines according to known methods, in particular, the electrical distance $D_{LA}$ to the surface of the medium to be measured. Determining a separating layer echo by means of the echo curve 901 from the measurement A is not possible, due to the existing emulsion. Furthermore, the reflections of the measurement B, which measurement is carried out by means of the coaxial guide 602, are acquired by the fill-level measuring device and are further analyzed in the form of a further digitized echo curve 702 in an evaluation unit 110. The evaluation unit 110 again determines the electrical distance $D_{LB}$ to the surface of the medium to be measured in the pipe B and the electrical distance $D_{IB}$ to the separating layer in the pipe B. Generally speaking, and in particular in the case of almost completely full containers, acquiring the bottom echo based on the amplitude ratios will not be possible, but it is also not mandatory in the context of this method.

Based on the values determined it is possible to draw the following conclusions relating to a virtual separating layer in the container, which separating layer would form after complete de-mixing of the emulsion, with the position of said separating layer being able to be determined according to the following equation:

$$d_{IA} = \frac{1}{\sqrt{\varepsilon_L \cdot \mu_L}} \cdot \left(\frac{D_{LA} - \kappa \cdot D_{LB}}{1 - \kappa}\right) + \frac{1}{\sqrt{\varepsilon_I \cdot \mu_I}} \cdot (D_{IB} - D_{LB})$$

Moreover, further characteristic values can be calculated that are required in the context of separating layer measuring and/or emulsion measuring. Examples of this include the level of the lower medium, the percentage composition of the emulsion contained in the container, the distribution of the media components in the container, the distribution of the mass components in the container (with the use of κ) or others in addition.

Apart from this, the method is also suitable for improving classical separating layer measuring. If in a container the filling conditions are such that there is only a small distance between the separating layer and the liquid surface (compare FIG. 4), then with the use of a device according to the invention it is possible to achieve a significant improvement in the accuracy of determining the position of the separating layer because the associated echo is not required for the evaluation. Furthermore, the present invention is associated with an advantage in that it can also correctly measure partial de-mixing of an emulsion.

FIGS. 10A to 10I show further exemplary embodiments of the invention. A characteristic and necessary feature always consists of the mandatory presence of a spatial area separate from the container, or at least of a sub-region in which a separating-layer echo position results that differs from the one in the container itself.

Exemplary embodiment 1001 (FIG. 10A) implements the method according to the invention by combining a fill-level measuring device according to the principle of the guided microwave 1002, which fill-level measuring device conveys its results from measuring by probe A by way of a communication line 1004 to a second measuring device 1003. The latter is designed, apart from measuring the measuring probe B 1004, to implement arithmetic linkage of the characteristic values determined, and to provide the results to the outside.

Exemplary embodiment 1011 (FIG. 10B) comprises a conventional radar fill-level measuring device 1012 that determines the results of a measurement A, an inventive fill-level measuring device 1013 according to the principle of the guided microwave that determines the result of a measurement B, and a higher-order control and evaluation unit 1014 that evaluates according to the invention the characteristic values determined in measurement A and measurement B and that provides said values to the outside.

Exemplary embodiment 1021 (FIG. 10C) shows a further variant. In this embodiment measurement A is implemented by means of a fill-level measuring device 1022 according to the principle of the guided microwave, and measurement B is implemented by means of a conventional radar device 1023 that acquires the position of the feed material surface and the position of a separating layer in a standpipe 1024 according to the invention. The higher-order control and evaluation unit 1025 in turn evaluates the results of the two measurements and provides them to the outside.

Exemplary embodiment 1031 (FIG. 10D) shows a further variant. The coaxial standpipe 1032 according to the invention is used in the interior to acquire the characteristic values of a measurement B, and is furthermore used as a rod probe on the outer surface of which a measurement A can be carried out according to the principle of the guided microwave. This embodiment is, in particular, advantageous in that only one process opening in the container 1033 is used by the fill-level measuring device 1034 according to the invention.

The interior of the measuring probe of the exemplary embodiment 1041 (FIG. 10E) comprises a coaxial standpipe according to the invention (comparable to that of reference character 1004) in which coaxial standpipe measurement B is carried out. Furthermore, according to the patent specification: "Device for double fill-level measuring according to a transit time method" this probe has been supplemented by an outer jacket pipe 1042 that comprises holes 1043 regularly spaced apart from each other, thus forming a double coaxial probe. In this arrangement measurement A takes place in the outer coaxial guide that uses the standpipe 1004 as the inner guide.

In many containers in the chemical industry separately arranged bypass pipes are used to determine the fill level. Exemplary embodiment 1051 (FIG. 10F) shows such an arrangement. The actual container 1052 comprises a bypass pipe 1053 that is arranged in parallel and that at its upper end and near the container bottom comprises connections (603, 604) to the container. The arrangement designed in this manner can, for example, be supplemented with two radar fill-level measuring devices 1054, 1055 which carry out the measurements A and B, and with a higher-order control and evaluation unit 1056 in such a manner that a device according to the invention for measuring separating layers and/or emulsions arises.

All the exemplary embodiments shown above share a common feature in that they only show exemplary arrangements. It may always be possible to implement according to different principles the measuring devices A and B that are used. Furthermore, it may be possible to use a separate evaluation unit or an evaluation unit which is present in at least one of the two devices A and B. Moreover, it may always be possible to combine two probes or two measuring methods in a single device.

Figure 10A:
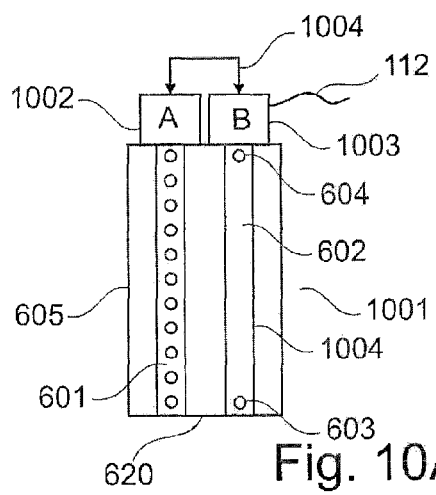
FIGS. 10A to 10I show measuring devices according to exemplary embodiments of the invention.
Figure 10D:
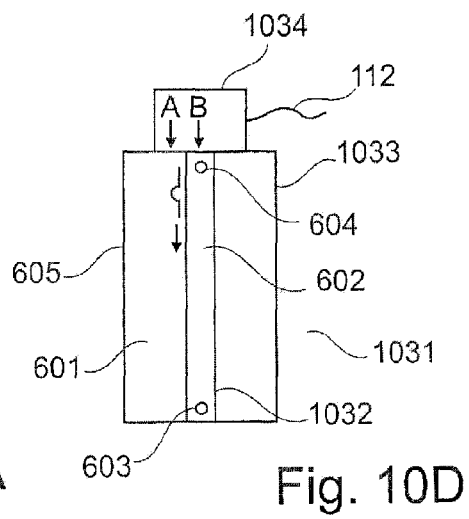
Figure 10B:
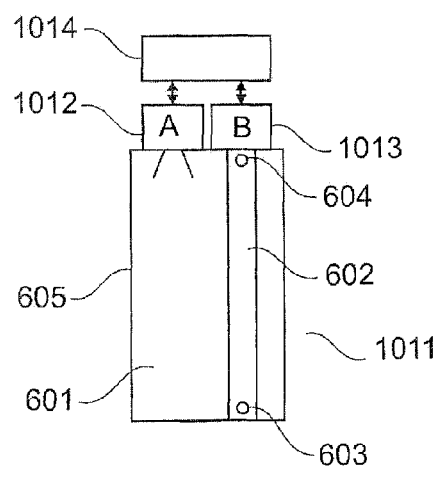
Figure 10E:
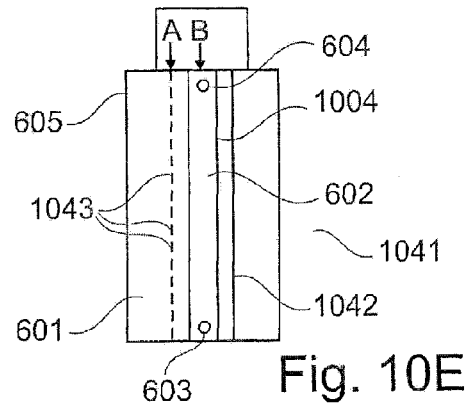
Figure 10C:
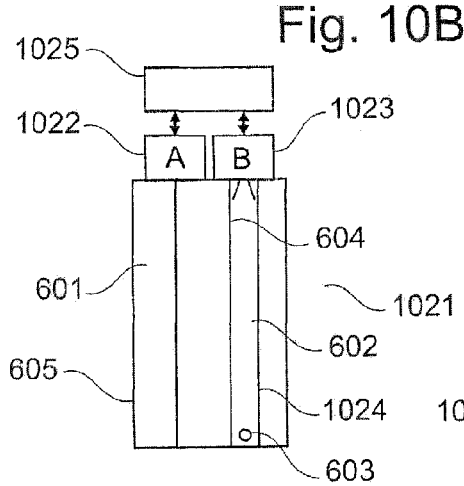
Figure 10F:
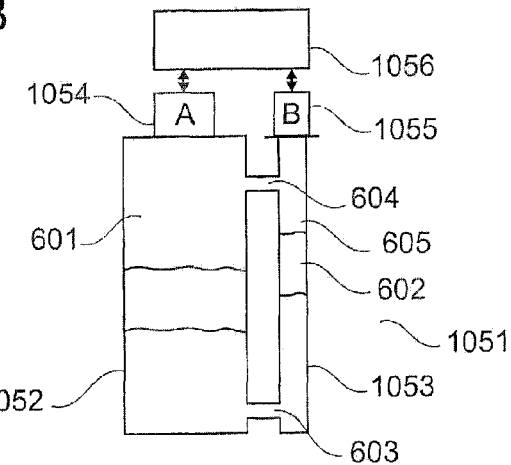
Figure 10G:
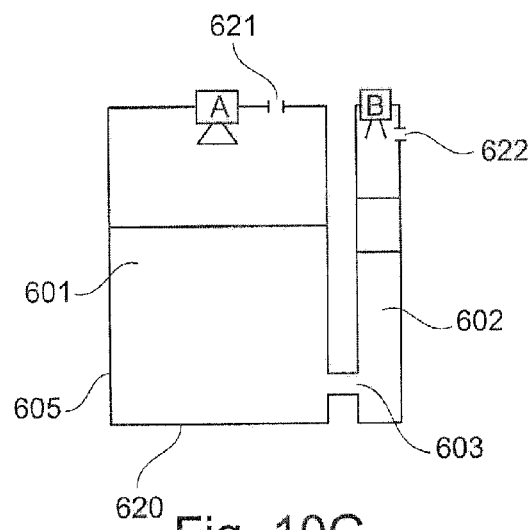

In the exemplary embodiment of FIG. 10G the first sub-region 602 and the second sub-region 601 are interconnected only by a connection 603 arranged near the container bottom 620. For pressure equalization the two sub-regions 601, 602 comprise, for example, valves 621, 622 that are arranged at the top of the container.

Figure 10I:
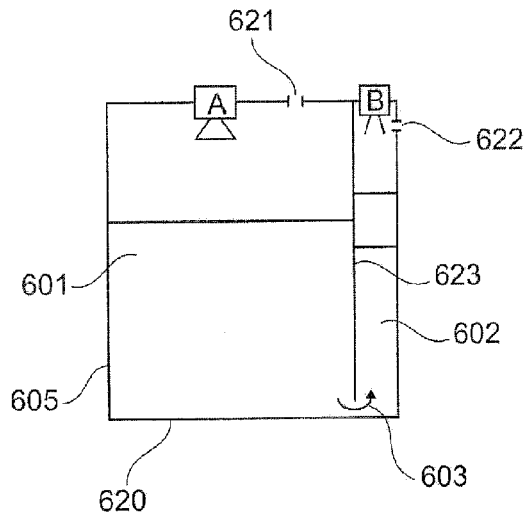
Figure 10H:
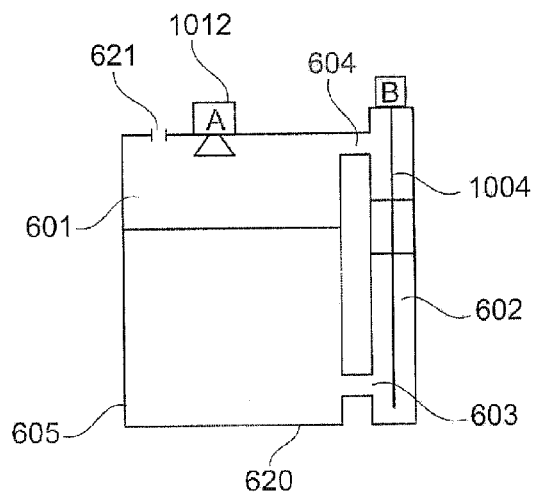

In the exemplary embodiment of FIG. 10H the two sub-regions are interconnected both by way of a lower connection 603 and by way of an upper connection 604, and the second sub-region 601 (but not the first sub-region 602) comprises a valve 621 for pressure equalization.

In the exemplary embodiment of FIG. 10I the two sub-regions 601, 602 are interconnected by way of a lower connection 603. The first sub-region 602 is not designed as a standpipe. Instead, the first sub-region is separated from the second sub-region by a planar partition wall 623. For fill-level measuring in the first sub-region 602 a fill-level radar can also be provided.

Figure 15:
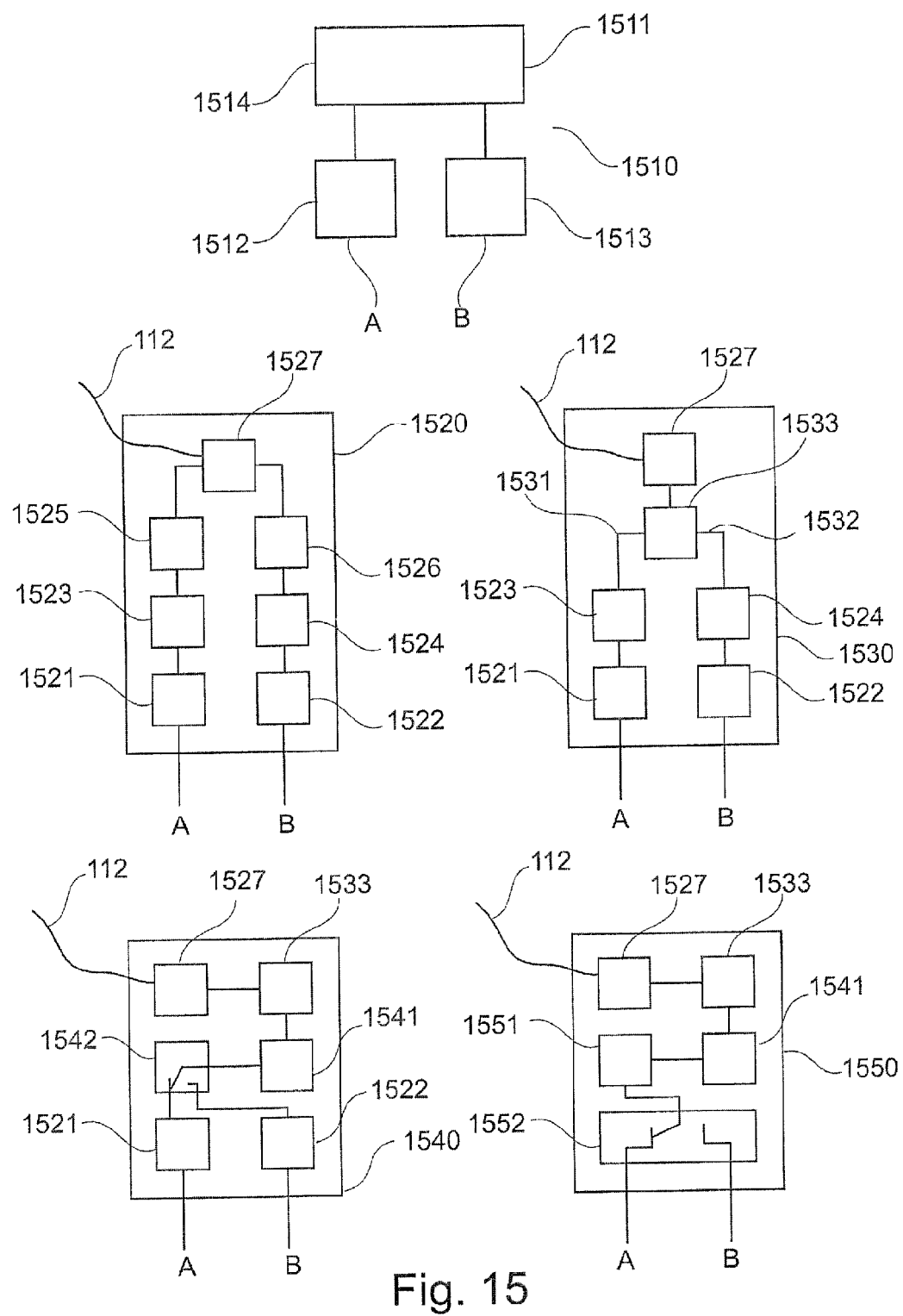
FIG. 15 shows the design of various electronic device setups relating to the measuring device according to an exemplary embodiment of the invention.

Furthermore, reference is made to the multitude of possible circuit designs of the measuring electronics of the devices for emulsion measuring, separating layer measuring or fill-level measuring. Examples of this are shown in FIG. 15. In contrast to the variants of various probes presented above, a few possible designs of corresponding device electronics are presented below. It should be noted that the probe connections of the hitherto presented probes are denoted in FIG. 15 by reference characters A and B.

It is possible for a device according to the invention to be implemented by combining two complete electronics modules 1512, 1513 of conventional fill-level measuring devices 101. The electronics modules may operate according to various principles suitable for designing the probe input couplings used at the connections A and B. A higher-order evaluation unit 1511 calculates the individual values, provided by the electronics modules 1512, 1513, relating to the position of the fill level and/or the position of the separating layer (from measurements A and B) and from them forms at least one measured value that is provided on an external interface 1514.

The illustration 1520 shows the design of a further electronics variant. The functionality of this variant corresponds to that of illustration 1510, wherein the high-frequency generating unit 1521, the analog-digital converter unit 1523, and the evaluation unit 1525 in combination are able to carry out a first measurement; and, furthermore, the high-frequency generating unit 1522, the analog-digital converter unit 1524, and the evaluation unit 1526 in combination are able to carry out a second measurement. The measured values determined from the measurements are offset against each other by a suitable program logic in the output unit 1527 and are provided towards the outside. It should be pointed out that in this structure measurement B can also be implemented according to an alternative measuring principle. The high-frequency unit 1522 then needs to be replaced by a suitable unit (laser generating unit, ultrasound generating unit).

A further exemplary embodiment according to illustration 1530 corresponds to that of illustration 1520, except that it utilizes a shared evaluation unit 1533 for evaluating the digitized echo curves provided on the connections 1531 and 1532.

Furthermore, it may also be possible to carry out signal conversion to digital representation with the use of a single analog-digital converter unit according to arrangement 1540. Apart from the analog-digital converter unit 1541, to this effect the device comprises an analog switch 1542 which conveys the analog low-frequency signals in a time division multiplex to the analog-digital converter unit 1541.

Moreover, the arrangement 1550 advantageously utilizes the existing structure of an available high-frequency unit 1551 of a sensor, and supplements the aforesaid with a high-frequency modulator 1552. With this variant a particularly simple design of a device according to the present invention can be achieved.

Furthermore, with many containers used in the petrochemical industry it is desirable to exclusively acquire the position of a separating layer. Examples of this include mineral-oil storage containers in which a water-condensate layer that settles at the bottom is to be monitored.

Figure 13:
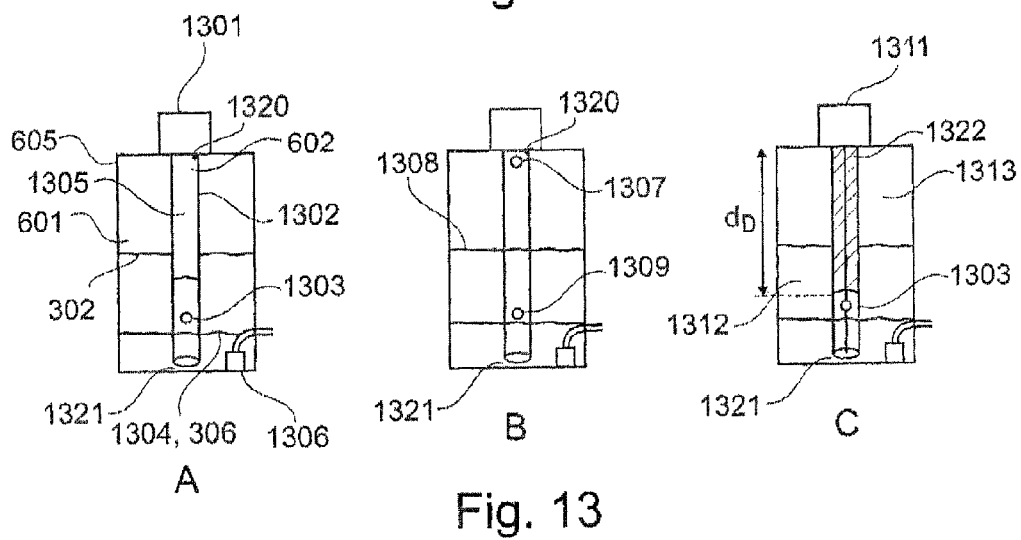
FIGS. 13A to 13C show devices for separating layer measuring and emulsion measuring.

FIG. 13 shows three devices according to the invention for separating layer measuring and/or emulsion measuring in sub-regions of a container.

The arrangement according to illustration (A) of FIG. 13 shows a fill-level measuring device according to a transit time method 1301, with the waveguide 1302 of said fill-level measuring device being open towards the bottom, and furthermore comprising a hole 1303 in the lower region of the waveguide. Depending on the type of the fill-level measuring device the waveguide can also be designed as a hollow guide or as a coaxial guide. The arrangement makes it possible to acquire a separating layer 1304 within the waveguide, wherein the level of this separating layer inside and outside the waveguide is identical. In addition, through the hole 1303 the upper medium flows in the waveguide, but in the waveguide does not rise to the level outside the waveguide, because the waveguide is closed towards the top, and the atmosphere 1305 contained therein is compressed by the rising liquid and builds up counterpressure. It may be possible, at the upper end of the waveguide, to acquire this pressure by means of a pressure sensor arranged above the fill medium in the first region, and from this deduce the level of the fill level. The values described above can also reliably be acquired during the formation of an emulsion, and can, for example, be used to control a condensate pump 1306.

The arrangement according to illustration (B) of FIG. 13 corresponds to the arrangement from illustration (A), and in addition on the upper end of the waveguide comprises a further hole 1307 that ensures that the level 1308 of the total fill level in the waveguide equals the level outside the waveguide. The arrangement is similar to the arrangement of FIG. 3, except that it utilizes the fact that the separating layer needs to be measured only in the lower region, and therefore a single hole 1309 for equalizing the level of the separating layer and of the medium inside and outside the waveguide is sufficient. There is no need to provide a multitude of holes along the waveguide, which can contribute to significantly improved reflection conditions within the waveguide. Generally speaking, the holes cause significant interference in the received signal.

The arrangement according to illustration (C) of FIG. 13 is entirely specialized for measuring a separating layer in the lower region of the waveguide. Since reflections up to a distance $d_D$ are of no interest (exclusive determination of the separating layer in the lower region of the container), the waveguide 1310 is designed in such a manner that no ingress of liquid into the interior of the waveguide in the region between the fill-level measuring device and a distance $d_D$ can occur. To this effect the probe can comprise a dielectric material, or it can comprise a seal. This arrangement is associated with a great advantage in that the signal of the fill-level measuring device 1311, which signal is used for measuring, along the direction of propagation up to a distance $d_D$ cannot be attenuated by the upper medium 1312 or by the overlay atmosphere 1313, nor can its propagation be influenced.

FIG. 13 thus shows measuring devices, in particular fill level-, separating layer- or emulsion measuring devices, that operate according to a transit time method. The devices comprise a container 605 for receiving a first liquid 606 and/or a second liquid 607 of lower density than the first liquid. The container comprises a first sub-region 602, a second sub-region 601 and at least two connections 1303, 1321 between the two sub-regions 601, 602 for exchanging liquid between the two sub-regions 601, 602 (see also FIG. 6).

The first sub-region 602 is formed by a waveguide which is at least in part arranged in the container 605, wherein in an upper region 1305 the waveguide is closed so that filling the second sub-region 601 with liquid 606, 607 results in a rise in pressure in the upper region.

Furthermore, a measuring device, in particular a fill-level measuring device or a separating-layer measuring device 1301, 1311 for acquiring an echo curve that images the reflection conditions within the waveguide is provided.

The evaluation unit, which is contained in the measuring device (not shown), is designed to determine at least one characteristic value relating to the position of the fill level and/or an actually existing or virtual separating layer between the two different liquids of the feed medium in the second sub-region 601, wherein the evaluation unit uses the echo curve for this.

According to a further exemplary embodiment the measuring device furthermore comprises at least one pressure gauge or a pressure measuring device 1320 in the upper region 1305, wherein the evaluation unit, which is contained in the measuring device, is designed for determining at least one characteristic value relating to the position of the total fill level and/or the position of an actually existing or virtual separating layer between the first and the second liquid in the second sub-region 601 by means of the pressure in the upper region 1305.

According to a further exemplary embodiment the waveguide 602 is a hollow guide.

According to a further exemplary embodiment the waveguide 602 is a coaxial waveguide.

According to a further exemplary embodiment the measuring device 1301, 1311 is a measuring device that emits an electromagnetic transmission signal or an acoustic transmission signal.

According to a further exemplary embodiment the measuring device is a device 1301, 1311 that operates according to the principle of the guided microwave and comprises an inner guide 104 (see FIG. 1) that is arranged inside the first sub-region 602, wherein the inner guide 104 and a wall of the first sub-region 602 form a coaxial guide so that the fill level within the first sub-region 602 is determined by means of the coaxial guide formed by the inner guide and the wall of the first sub-region.

According to a further exemplary embodiment the measuring device furthermore comprises a dielectric material 1322 or a seal in the upper region 1305 which prevents the first and/or the second liquid from entering the second region.

Furthermore, a method for emulsion measuring is stated, with the method comprising the following steps:

filling a first liquid 606 and/or a second liquid 607 of lower density than the first liquid in a second sub-region of a container 605 that comprises a first sub-region 602, a second sub-region 601 and at least two connections 1303, 1321 between the two sub-regions 601, 602 for exchanging liquid between the two sub-regions 601, 602;

wherein the first sub-region 602 is formed by a waveguide that is at least in part arranged in the container 605;

increasing the pressure in an upper region 1305 of the waveguide 602, because the waveguide 602 is closed in the upper region 1305;

acquiring an echo curve that images the reflection conditions within the waveguide 602;

determining a characteristic value relating to the position of the fill level and/or an actually present or virtual separating layer between the two different liquids of the feed medium in the second sub-region 601 with the use of the echo curve.

Furthermore, the following steps may be provided:

determining the pressure in the upper region (1305) of the waveguide;

determining at least one characteristic value relating to the total fill level of the first and/or the second liquid in the second sub-region (601) by means of the pressure in the upper region (1305).

Figure 14:
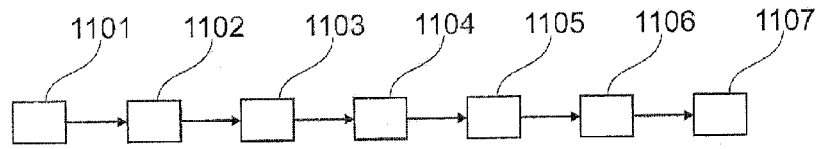
FIG. 14 shows a flow chart of a method according to an exemplary embodiment of the invention.

FIG. 14 shows a flow chart of a method according to an exemplary embodiment of the invention. In step 1401 determining the total fill level as well as determining the position of the separating layer between the two liquids located in the container takes place in the first sub-region of the container.

In step 1402 determining the total fill level as well as determining the position of the separating layer between the two liquids located in the container takes place in the second sub-region of the container. In step 1403 the ratio of the densities of the two liquids is calculated. In step 1404 the liquids in the second sub-region of the container are agitated so that an emulsion forms, and in step 1405 the addition of a further quantity of liquid to the second sub-region of the container takes place. In step 1406 again the acquisition and evaluation of an echo curve in each case in the first sub-region and in the second sub-region take place. From the two measured values, obtained in this manner, of the first sub-region and from the one measured value (total fill level) of the second sub-region of the container, subsequently in step 1407 with the knowledge of the density ratio of the two liquids the position of the virtual separating layer or of the mixing ratio is calculated. In this process it is important that the two total fill levels are at different levels.

In addition, it should be pointed out that "comprising" does not exclude other elements or steps, and "a" or "an" does not exclude a plural number. Furthermore, it should be pointed out that characteristics or steps which have been described with reference to one of the above exemplary embodiments can also be used in combination with other characteristics or steps of other exemplary embodiments described above. Reference characters in the claims are not to be interpreted as limitations.

The invention claimed is:

1. A measuring device operating according to a transit time method, comprising:

a container holding a fill medium which comprises a first liquid and a second liquid of lower density than the first liquid, the container includes a first sub-region, a second sub-region and at least one connection between the first and second sub-regions, the connection configured to exchange liquid between the first and second sub-regions;

a first measuring apparatus acquiring a first echo curve that illustrates the reflection conditions within the first sub-region;

a second measuring apparatus acquiring at least one second echo curve that illustrates the reflection conditions within the second sub-region; and an evaluation unit:
  determining a first characteristic value of the first echo curve relating to the fill level of the two liquids;
  determining a second characteristic value of the first echo curve relating to the position of a separating layer between the two liquids in the first sub-region of the container;
  determining a third characteristic value of the second echo curve relating to the fill level of the two liquids in the second sub-region of the container; and
  calculating at least one fourth characteristic value relating to the position of a virtual separating layer between the two liquids in the second sub-region,
  wherein the evaluation unit uses the first and second characteristic values of the first echo curve and the third characteristic value of the second echo curve.

2. The measuring device according to claim 1, wherein the first sub-region is formed by the interior space of a standpipe.

3. The measuring device according to claim 1, wherein the first sub-region is formed by a bypass pipe of the container.

4. The measuring device according to claim 1, wherein the connection between the two sub-regions is formed by a first opening in the first sub-region of the container situated near the container bottom, and by a second opening in the first sub-region of the container, which second opening in the case of a properly filled container is situated above the feed medium.

5. The measuring device according to claim 1, wherein the first sub-region and the connection are configured in such a manner that when a defined quantity of liquid is added in the second sub-region the level of a liquid column forming in the first sub-region differs from the level of a liquid column in the second sub-region.

6. The measuring device according to claim 1, wherein the first measuring apparatus and the second measuring apparatus are identical devices.

7. The measuring device according to claim 1, wherein at least one of the first and the second measuring apparatus is a measuring apparatus that emits an electromagnetic transmission signal or an acoustic transmission signal.

8. The measuring device according to claim 1, wherein the first measuring apparatus operates according to the principle of the guided microwave and comprises an inner guide arranged within the first sub-region and wherein the inner guide and a wall of the first sub-region form a coaxial guide so that the echo curve within the first sub-region is determined by means of the coaxial guide formed by the inner guide and the wall of the first sub-region.

9. The measuring device according to claim 1, wherein the measuring device is configured to acquire and issue at least one characteristic value relating to the fill level in the second sub-region.

10. The measuring device according to claim 1, wherein the evaluation unit determines one of (a) the at least one characteristic value relating to the position of an actually existing or virtual separating layer between two different liquids of the feed medium in the second region and (b) the at least one characteristic value relating to the composition of the mixture comprising the two different liquids takes place without the aid of capacitive measuring.

11. A method for at least one of an emulsion measuring and a separating layer measuring, comprising the following steps:
  mixing two different liquids in a first sub-region of a container;
  determining at least one first characteristic value relating to the fill level of the two different liquids, and determining at least one second characteristic value relating to the position of a separating layer between the two liquids in a second sub-region of the container;
  determining at least one third characteristic value relating to the fill level of the two liquids in the first sub-region of the container; and
  calculating at least one fourth characteristic value relating to the position of an actually existing or virtual separating layer between the two liquids in the first sub-region of the container with the use of the first, second, and third characteristic values as well as with the use of the density ratio of the two liquids.

12. The method according to claim 11, further comprising the step of:
  determining the density ratio of the two liquids by means of a measurement, in which the at least one characteristic value relating to the fill level of the two different liquids and at least one characteristic value relating to the position of the separating layer between the two liquids in the first and the second sub-regions of the container is determined.

13. The method according to claim 11, wherein the method is carried out by a measuring device, the device including:
  the container holding a fill medium which comprises the two liquids, a first one of the liquids having a higher density than a second one of the liquids, the container including at least one connection between the first and second sub-regions, the connection configured to exchange liquid between the first and second sub-regions;
  a first measuring apparatus acquiring a first echo curve that illustrates the reflection conditions within the first sub-region;
  a second measuring apparatus acquiring at least one second echo curve that illustrates the reflection conditions within the second sub-region; and
  an evaluation unit performing the determining steps and the calculating step.

14. The method according to claim 12 wherein the mixing of the two liquids in the second sub-region is performed after the density ratio of the two liquids has been determined.

* * * * *